(12) United States Patent
Bier

(10) Patent No.: US 7,282,127 B2
(45) Date of Patent: Oct. 16, 2007

(54) MICROCAPILLARY DEVICES USING HIGH DIELECTRIC CONSTANT MATERIALS AND RELATED METHODS

(75) Inventor: Martin Bier, Greenville, NC (US)

(73) Assignee: East Carolina, Greenville, NC (US)

( * ) Notice: Subject to any disclaimer, the term of this patent is extended or adjusted under 35 U.S.C. 154(b) by 127 days.

(21) Appl. No.: 11/101,215

(22) Filed: Apr. 7, 2005

(65) Prior Publication Data
US 2005/0224353 A1    Oct. 13, 2005

Related U.S. Application Data

(60) Provisional application No. 60/561,755, filed on Apr. 13, 2004.

(51) Int. Cl.
*G01N 27/26* (2006.01)
(52) U.S. Cl. .................. 204/454; 204/458; 204/457; 204/609; 204/608
(58) Field of Classification Search ................ 204/451, 204/454, 601, 457, 458, 608, 609
See application file for complete search history.

(56) References Cited

U.S. PATENT DOCUMENTS

| | | | | |
|---|---|---|---|---|
| 4,908,112 | A | * | 3/1990 | Pace ...................... 210/198.2 |
| 5,126,022 | A | * | 6/1992 | Soane et al. ................. 204/458 |
| 5,151,164 | A | * | 9/1992 | Blanchard et al. ........... 204/451 |
| 5,262,031 | A | * | 11/1993 | Lux et al. .................... 204/601 |
| 5,286,434 | A | * | 2/1994 | Slater et al. ................. 204/457 |
| 5,750,015 | A | * | 5/1998 | Soane et al. ................. 204/454 |
| 5,800,690 | A | * | 9/1998 | Chow et al. ................. 204/451 |
| 5,880,071 | A | * | 3/1999 | Parce et al. .................. 204/453 |
| 6,001,266 | A | | 12/1999 | Bier ........................... 210/748 |
| 6,013,166 | A | * | 1/2000 | Heller ......................... 204/469 |
| 6,120,665 | A | * | 9/2000 | Chiang et al. .............. 204/450 |
| 6,277,258 | B1 | * | 8/2001 | Ivory et al. ................. 204/450 |
| 6,749,735 | B1 | * | 6/2004 | Le Febre .................... 204/601 |
| 6,805,783 | B2 | * | 10/2004 | Ohkawa ...................... 204/454 |
| 7,081,189 | B2 | * | 7/2006 | Squires et al. .............. 204/451 |
| 2002/0187503 | A1 | * | 12/2002 | Harrold et al. ................ 435/6 |
| 2003/0127329 | A1 | * | 7/2003 | DeVoe et al. ............... 204/454 |
| 2003/0180449 | A1 | * | 9/2003 | Wiktorowicz et al. ........ 427/97 |

OTHER PUBLICATIONS

Fishbane et al., Physics for Scientists and Engineers, Prentice-Hall, Inc. (1993) p. 772, Table 26-1.*
Fuhr et al., Microfabricated Electrohydrodynamic (EHD) pumps for liquid of higher conductivity, (1992) Journal of microelectromechanical systems, vol. 1, No. 3, pp. 141-146.*

(Continued)

*Primary Examiner*—Nam Nguyen
*Assistant Examiner*—Surekha Vathyam
(74) *Attorney, Agent, or Firm*—Myers Bigel Sibley & Sajovec, P.A.

(57) ABSTRACT

A microcapillary device includes a microcapillary tube. An anode is positioned at a first end of the microcapillary tube. A cathode is positioned at a second end of said microcapillary tube. A plurality of electric field reducing components are spaced apart along a length of the microcapillary tube. The anode and the cathode generate an electric field along the length of the microcapillary tube, and the plurality of electric field reducing components selectively reduce the electric field at spatial intervals along the length of the microcapillary tube.

22 Claims, 7 Drawing Sheets

OTHER PUBLICATIONS

Xu "Tutorial: Capillary Electrophoresis" (1996) The Chemical Educator, vol. 1 (2) ,pp. 1-14.*

Philibert "One and a Half Century of Diffusion: Fick, Einstein, Before and Beyond" (2006) Diffusion Fundamentals, vol. 4, pp. 6.1-6.19.*

Bier, Martin, "Brownian ratchets in physics and biology", *Contemporary Physics*, 1997, vol. 38, No. 6, pp. 371-379.

Lenne et al., "Flow Profiles and Directionalitiy in Microcapillaries Measured by Flourescence Correlation Spectroscopy", Single Mo. 3 (2002) 4, pp. 194-200.

Fishbane et al. "Table 26-, Dielectric Properties of Various Materials" *Physics for Scientists and Engineers*, Prentice Hall, Inc. p. 772 (1993).

International Search Report and Written Opinion for PCT/US05/12428; date of mailing Dec. 11, 2006.

* cited by examiner

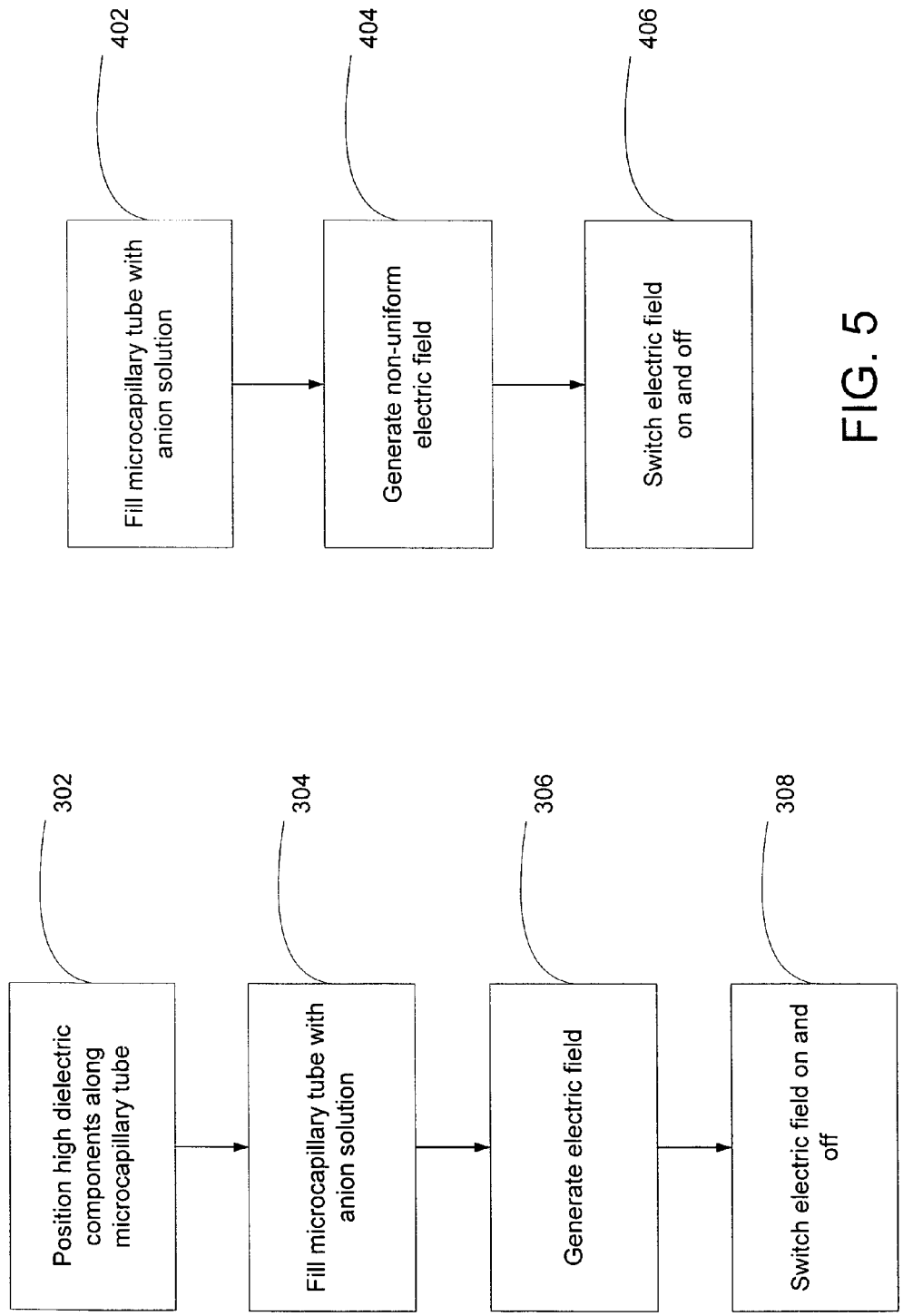

MICROCAPILLARY DEVICES USING HIGH DIELECTRIC CONSTANT MATERIALS AND RELATED METHODS

RELATED APPLICATIONS

This application claims priority to U.S. Provisional Application Ser. No. 60/561,755, filed Apr. 13, 2004, the disclosure of which is hereby incorporated by reference in its entirety.

BACKGROUND OF THE INVENTION

1. Field of the Invention

The present invention relates to methods and devices for separating analytes in a solution using microcapillary devices.

2. Background

Various types of separation techniques are available for separating analytes in a solution. For example, flat-plate electrophoretic gel methods have been used to separate DNA components for the base sequencing of DNA. This method typically involves a gel that is sandwiched between two glass plates. DNA in the gel sample migrates electrophoretically by applying a voltage across both ends of the glass plates. Other methods for separating biological samples, such as DNA, include capillary electrophoretic devices. In these devices, the sample is placed in a gel. The gel is placed in capillaries typically made of silica or quartz. A sample migrates electrophoretically when a voltage is applied across the length of the capillary or capillary array assembly. Other methods and devices for separating analytes are discussed in U.S. Pat. No. 6,001,266, the disclosure of which is hereby incorporated by reference in its entirety.

In silica or quartz microcapillaries, ionized silanol groups (Si—OH) generally congregate on the inner surface of the capillary wall. The negatively charged surface can be balanced by a sheath of counter ions, such as $H_3O^+$ from the buffer, to form an electric double layer. When an electric field is applied along the length of the microcapillary, the positive ions in the diffuse part of the liquid migrate to the electrode of opposite polarity (generally the cathode). Liquid within the electric double layer is entrained by the migrating ions. The resulting "plug-like" flow, or electroosmotic flow, transports analytes dissolved in the liquid. Charged analytes can then separate electrophoretically. Depending on charge, solvation, and mass, the electric field will cause the analytes to migrate at different rates as they move toward the anode.

Biomolecules, such as DNA strands and proteins, generally carry a negative charge. At greater pH values, such as a pH value of more than three, the electrophoretic force on an anion towards the anode is generally weaker than the drag force of the buffer's electroosmotic flow toward the cathode. At lower pH values, such as lower than three, the anions generally migrate toward the anode.

Because the above separation process in a microcapillary depends on charge, solvation, and mass, certain analytes in a solution may not separate from one another. For example, an analyte that is twice as large and has twice as much charge as another analyte may travel at the same speed. That is, an increase in friction due to an increase in size of one analyte compared to another may slow its speed; however, if the analyte also has an increased charge, its speed may be the same as the smaller analyte with a lower charge.

SUMMARY OF THE INVENTION

In some embodiments of the present invention, a microcapillary device is provided including a microcapillary tube. An anode is positioned at a first end of the microcapillary tube. A cathode is positioned at a second end of the microcapillary tube. A plurality of electric field reducing components is spaced apart along a length of the microcapillary tube. The anode and the cathode generate an electric field along the length of the microcapillary tube, and the plurality of electric field reducing components selectively reduce the electric field at spatial intervals along the length of the microcapillary tube.

In this configuration, the electric field can be switched on and off so that analytes in the microcapillary tube can migrate within the tube at a rate that is substantially independent of charge.

In certain embodiments, the plurality of electric field reducing components includes a plurality of high dielectric components. In some embodiments, the plurality of high dielectric components can include strontium titanate. The plurality of high dielectric components can be formed of a material having a dielectric constant of about 100. The plurality of high dielectric components can each form a circumferential ring around an outer surface of the microcapillary tube.

In certain embodiments, the plurality of electric field reducing components is a plurality of electrodes. The plurality of electrodes can include electrically conducting wires forming circumferential rings around an outer surface of the microcapillary tube.

In some embodiments, a controller is operatively connected to the anode and the cathode. The controller can be configured to generate the electric field between the anode and the cathode and to switch the electric field on and off in predetermined temporal activation/deactivation intervals. The controller can be configured to generate the electric field at a voltage in the range of about 1,000 V/m to about 30,000 V/m. The activation/deactivation intervals can have an activation and/or a deactivation duration of between about 0.1 ms and about 100 seconds.

The microcapillary tube can have a diameter of about 50 μm, the plurality of electric field reducing components can have a length along a primary axis of the microcapillary tube of about 0.1 mm, and the plurality of electric field reducing components can be separated by about 0.9 mm. The device can include a solution in the microcapillary tube comprising a fluid and a plurality of analytes. The fluid can be an aqueous fluid and the plurality of analytes can be selected from the group consisting of nucleic acids, amino acids, peptides, proteins, nucleosides and nucleotides, small organic compounds, inorganic ions, organic acids, vitamins, steroids, carbohydrates, hormones or drugs, and cells.

In some embodiments, methods of separating analytes in a microcapillary tube are provided. A plurality of electric field reducing components is spaced apart and positioned along a length of a microcapillary tube. The microcapillary tube is filled with an analyte solution. An electric field is generated along the length of the microcapillary tube. The plurality of electric field reducing components selectively reduce the electric field at spatial intervals along a length of the microcapillary tube. The electric field is switched on and off to separate a plurality of analytes in the analyte solution along the length of the microcapillary tube.

The switching step can include activating the electric field for an activation duration of between about 0.1 ms and 100 seconds and deactivating the electric field for a deactivation duration of between about 0.1 ms and about 100 seconds. The generating step can include generating the electric field at a voltage in the range of about 1,000 V/m to 30,000 V/m or more.

The plurality of electric field reducing components can be a plurality of high dielectric components, which can be formed in a series of circumferential rings around an outer surface of the microcapillary tube. Positioning a plurality of electric field reducing components spaced apart along a length of a microcapillary tube can include coating the microcapillary tube with a high dielectric coating material, and selectively etching the coating material to provide the plurality of high dielectric components. Accordingly, portions of the coating material can be removed by selectively etching the material in a desired pattern.

In some embodiments, methods of manufacturing a microcapillary device include providing a microcapillary tube, coating the microcapillary tube with a high dielectric coating material, and selectively etching the coating material to provide a plurality of high dielectric components spaced apart along a length of the microcapillary tube. For example, as described above, portions of the coating material can be removed during the etching step.

In some embodiments, methods of separating analytes in a microcapillary tube include filling the microcapillary tube with an analyte solution, generating a non-uniform electric field along a length of a microcapillary tube, and switching the non-uniform electric field on and off to separate a plurality of analytes in the analyte solution.

BRIEF DESCRIPTION OF THE DRAWINGS

FIGS. 4-6 are flowcharts illustrating operations according to embodiments of the present invention.

DETAILED DESCRIPTION OF THE INVENTION

Figure 1A:
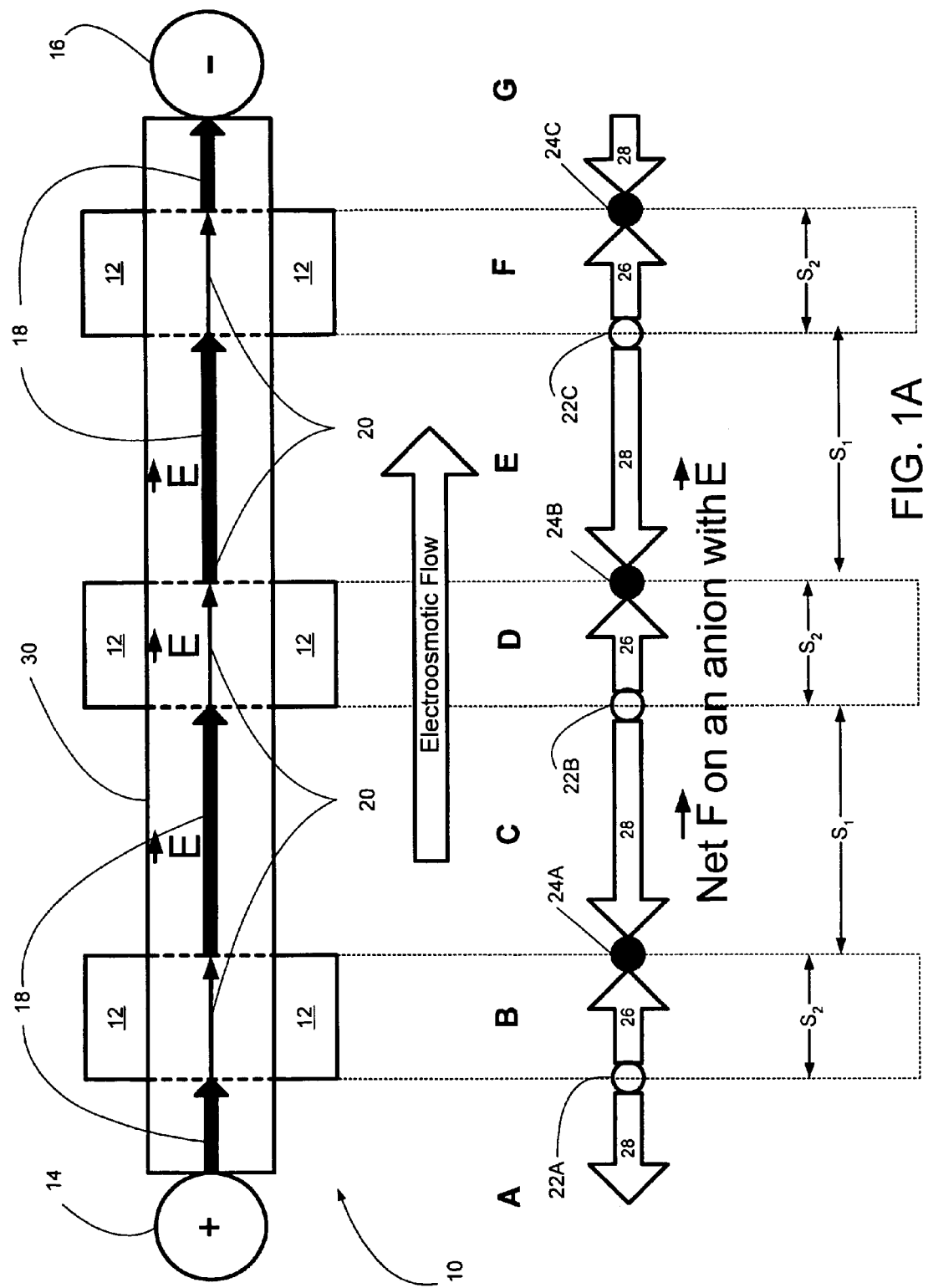
FIGS. 1A-1B are a microcapillary devices according to embodiments of the present invention.

The present invention now will be described more fully hereinafter with reference to the accompanying drawings, in which various embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the relative sizes of elements may be exaggerated for clarity. Like reference numerals in the drawings denote like members.

When an element is described as being formed "on" or "adjacent to" another layer or element, the element may be formed directly on the other layer or element, or other elements or layers may be interposed therebetween. In contrast, when an element is referred to as being "directly on" another element, there are no intervening elements present. The thicknesses of elements, layers or regions may be exaggerated for clarity.

"Analytes" as used herein means any suitable analyte, including, but not limited to, amino acids, peptides, proteins, nucleosides and nucleotides (this term including oligonucleotides and including DNA and RNA), small organic compounds, inorganic ions, organic acids, vitamins, steroids, carbohydrates, hormones or drugs (e.g., steroids, antiviral compounds, amphetamines, anti-depressants, and other psychoactive drugs, antimicrobial compounds, antineoplastic compounds, etc.), cells (including live and dead cells; including plant, animal, and bacterial, yeast, protozoa, algae, and other microbial cells).

Embodiments according to the present invention provide devices and methods for separating analytes in a solution in a microcapillary tube or microcapillary tube array. Referring to FIG. 1A, a microcapillary device 10 includes a microcapillary tube 30 having an anode 14 at one end and a cathode 16 at the other end. High dielectric constant rings 12 are spaced apart along the length of the microcapillary tube 30. The high dielectric rings 12 have a width $S_2$ and are separated by a distance $S_1$. The analytes can be in an aqueous fluid solution.

In this configuration, analytes may be separated from one another. An electric field $\vec{E}$ can be generated along the length of the microcapillary tube 30. The electric field $\vec{E}$ is reduced in regions near the high dielectric constant rings 12.

In summary, the reduced electric field $\vec{E}$ results in regions B, D and E in which the net force on an analyte in the microcapillary tube 30 is dominated by the electrophoretic force toward the cathode 16 and other regions A, C, E, and G in which the net force is dominated by the electric field $\vec{E}$ toward the anode 14 (for an anion). These forces are described further below. These opposing net forces can create stable positions 24A-24C and unstable positions 22A-22C for analytes in the microcapillary tube 30. When the electric field $\vec{E}$ is turned off, the net force on an analyte is zero, and the analytes in the microcapillary tube 30 diffuse at a rate that is based primarily on size. The electric field $\vec{E}$ can be turned on and off such that, on average, analytes migrate in one direction. The rate at which the analytes migrate is substantially independent of charge and may be based primarily on the diffusion rate. Therefore, analytes can be separated based on size and substantially independent of charge.

As illustrated in FIG. 1A, a strong portion 18 of the electric field $\vec{E}$ is present in regions A, C, E, and G and a weak portion 20 of the electric field $\vec{E}$ is present in regions B, D and F. Both portions 18, 20 of the electric field $\vec{E}$ are in the direction of the cathode 16, which results in a force on an anion that is toward the anode 14. In contrast, the electroosmotic flow is in the direction of the cathode 16 and provides an opposing force on an anion towards the cathode 16. The net force $\vec{F}$ on certain analytes in the electric field $\vec{E}$ is illustrated by two forces in opposite directions: 1) a net force 28 in regions A, C, E, and G toward the anode 14; and 2) a net force 26 in regions B, D and E towards the cathode 16 (corresponding to regions of the microcapillary tube 30 that have a reduce electric field $\vec{E}$ (weak portion 18) due to the high dielectric rings 12). Although electroosmotic flow towards the cathode 16 is present along substantially the entire length of the microcapillary tube 30, the net force 28 is dominated by the strong portion 18 of the electric field $\vec{E}$ forcing an anion towards the anode 14. On the other hand, the net force 26 is dominated by electroosmotic flow because of the low electric field strength of the weak portion 20 of the electric field $\vec{E}$.

As shown in FIG. 1A, the net forces 26 and 28 result in unstable positions 22A-22C and stable positions 24A-24C for analytes in the microcapillary tube 30. That is, the net forces 26 and 28 on an analyte each provide a force away from the unstable positions 22A-22C and toward the stable positions 24A-24C. If the electric field $\vec{E}$ is on for a period of time, the analytes in the microcapillary tube 30 generally migrate towards the stable positions 24A-24C. When the electric field $\vec{E}$ is switched off, the electroosmotic flow ceases and analytes may diffuse freely along the length of the microcapillary tube 30. That is, the net forces 26 and 28, the unstable positions 22A-22C and the stable positions 24A-24C are no longer active in the absence of the electric field $\vec{E}$ and the net force on an analyte is approximately zero. Without wishing to be bound by any particular theory, in the absence of the electric field $\vec{E}$, analytes can diffuse randomly along the length of the microcapillary tube 30 due to Brownian motion that is substantially based on size. Smaller analytes typically diffuse faster than larger analytes. For example, a single aminoacid may diffuse faster than a dimer of two aminoacids, and likewise, a monosaccharide may diffuse faster than a disaccharide. The electric field $\vec{E}$ can be switched on and off so that the forces on the analytes alternate between two conditions 1.) a net force towards the stable positions 24A-24C when the electric field $\vec{E}$ is on and 2.) a net force of approximately zero and free diffusion when the electric field $\vec{E}$ is off.

In some embodiments, the microcapillary device 10 can be used to separate analytes based on their diffusivity by switching the electric field $\vec{E}$ on and off. The electric field $\vec{E}$ of the microcapillary device 10 can be switched on and off in a series of cycles such that one cycle of the system lasts T=$t_{on}$+$t_{off}$ where $t_{on}$ is the duration of the time period in which $\vec{E}$ is switched on, and $t_{off}$ is the duration of the time period in which $\vec{E}$ is switched off. For each cycle T, there is some probability that any particular analyte will travel from one (or more) of the stable positions 24A-24C to another of the stable positions 24A-24C to the left. If the distance $S_1$ is greater than the distance $S_2$, then the probability that the analyte will travel to one of the stable positions 24A-24C to the right is lower than the probability that the analyte will travel to one of the stable positions 24A-24C to the left. In certain embodiments, the distances S1 and S2 can be selected so that the probability that an analyte will move in the less likely direction is effectively zero.

Figure 2:
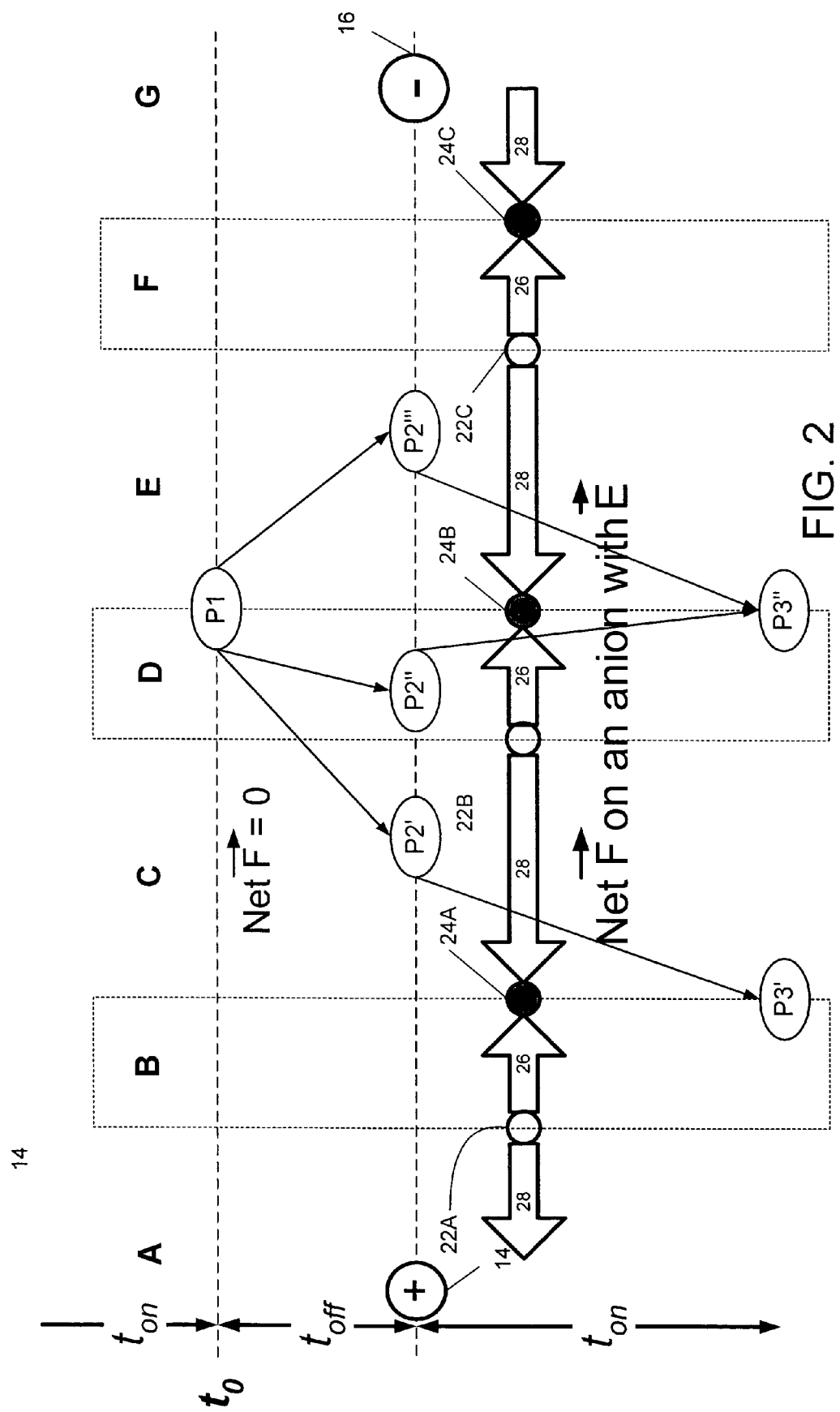
FIG. 2 is a force diagram of exemplary positions of an analyte in the microcapillary tube of FIG. 1A when the electric field is switched on and off.

Examples of initial and subsequent positions of an analyte in the microcapillary tubes 30 of FIG. 1A in a fluctuating electric field $\vec{E}$ are shown in FIG. 2. As illustrated, an analyte has a net force $\vec{F}$ when the electric field $\vec{E}$ is on (during $t_{on}$) and a net force $\vec{F}$ of approximately zero when the electric field $\vec{E}$ is off (during $t_{off}$). When the electric field $\vec{E}$ is on, the net force $\vec{F}$ is toward the anode in regions A, C, E, and G, and toward the cathode in regions B, D, and F.

In particular, as illustrated in FIG. 2, an analyte has a starting position P1, which corresponds to stable position 24B when the electric field $\vec{E}$ is on. The electric field $\vec{E}$ is then turned off for time $t_{off}$. During $t_{off}$, the analyte diffuses along the microcapillary tube, and the analyte has some probability of being located at a second position some distance to the right or left of P1. Without wishing to be bound by theory, it is believed that the probability of motion is a result of the Brownian motion of the analyte during $t_{off}$. Exemplary second positions P2' in region C, P2" in region D, and P2'" in region E are shown. In the example illustrated in FIG. 2, the microcapillary device can be tuned such that the probability that an analyte will diffuse from the starting position P1 into other regions (e.g., regions A, B, F or G) that are further away from P1 than regions C, D, or E is low. For example, the $t_{off}$ duration can be adjusted so that this probability is low.

If the analyte's second position after time $t_{off}$ is P2' and the electric field $\vec{E}$ is switched on for time $t_{on}$, the analyte will be acted on by net force 28 in the direction of the anode 14. If $t_{on}$ is sufficiently long, the analyte will be positioned at P3' after time $t_{on}$. Position P3' is aligned with stable position 24A. However, if the analyte's second position after time $t_{off}$ is P2" or P2'", the analyte will be acted on by net forces 26 and 28, respectively toward stable position 24B. If $t_{on}$ is sufficiently long, analytes at positions P2" or P2'" can migrate to position P3", which is aligned with stable position 24B. Although exemplary positions P2', P2", and P2'" are shown in FIG. 2, it should be understood that a microcapillary device can be configured and $t_{on}$ selected such that any analyte in regions D and E will migrate to position P3" and any analyte in region C will migrate to position P3' when the electric field $\vec{E}$ is on.

As illustrated, an analyte is more likely to migrate to the left or return to its starting position than it is likely to migrate to the right. As would be understood by those of skill in the art, diffusing a longer distance is more likely for some analytes (e.g., monomers) than it is for larger analytes (e.g., polymers). Therefore, the electric field $\vec{E}$ can be repeatedly turned on and off as discussed with respect to the example in FIG. 2 such that analytes may be transported towards the anode at a rate that is based on size, i.e., so that small analytes are transported faster than larger analytes.

In some embodiments, the microcapillary device 10 of FIG. 1A is configured such that S1 is between about 1 mm and 1 µm and S2 is between about 1 mm and 1 µm. In more particular embodiments, S2 is about 10 times shorter than S1. The high dielectric rings 12 can be formed of any suitable material for decreasing the electric field, including high dielectric materials, such as strontium titanate and barium titanate, having a dielectric constant of greater than about 80. In particular embodiments, the high dielectric material is a material that does not polarize or form a permanent dipole because such a dipole field could interfere with the free diffusion of the analytes when the electric field $\vec{E}$ is off. The high dielectric rings 12 can have cover a length along the microcapillary tube 30 of between about 0.1 µm and about 0.1 mm. The dielectric rings 12 can have a thickness of about 100 µm extending away from the microcapillary tube 30. The voltage between the anode 14 and the cathode 16 when the electric field is on can be between about 1000 volts. For calculations of analyte velocities in an electric field are given, for example, see P. F. Lenne, D. Colombo, H. Giovannini, and H. Rigneault, *Flow Profiles and Directionality in Microcapillaries Measured by Fluroescence Correlation Spectroscopy*, Single Mol. 3 (2002) 4, 194-200. These calculations can be used to determine appropriate voltages, desired analyte velocities in the electric field, and the like. For example, if a microcapillary tube is 10 cm and is placed in an electric field of 100 V/cm (e.g., between two capacitor plates having a potential difference of 1000 V), the speed of the analyte is about 0.17 mm/s. However, at lower pH values (e.g., at pH values less than 7), the speed may decrease.

Figure 1B:
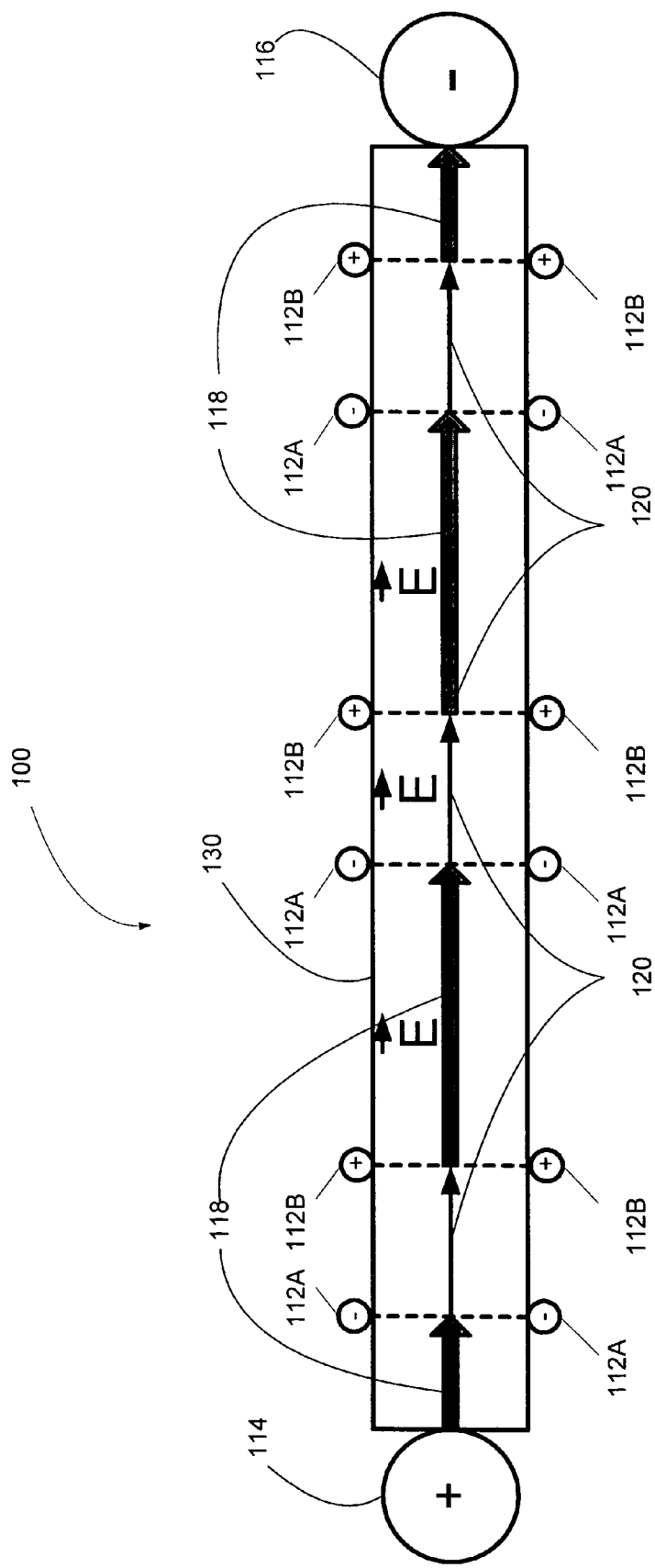

Other configurations of microcapillary devices can be used to form a non-uniform electric field in the microcapillary. For example, as shown in FIG. 1B, a microcapillary device 100 includes a microcapillary tube 130 having an anode 114 at one end and a cathode 116 at the other end. Electrodes 112A-112B are spaced apart along the length of the microcapillary tube 130. As illustrated, electrodes 112A-112B are electrically conducting wires wrapped around the circumference of the microcapillary tube 130. Electrodes 112A have a negative charge and alternate with electrodes 112B, which have a positive charge. Therefore, the electrodes 112A-112B are spaced to selectively reduce the electric field formed between the anode 114 and the cathode 116 so that the resulting electric field $\vec{E}$ includes a strong portion 118 and a weak portion 120.

In some embodiments, the electrodes 112A-112B are wires having a diameter of about 25 micrometers and can be positioned so that each positive and negative wire pair is spaced about 0.1 mm from one another. For example, a microcapillary tube 130 having an inner diameter of about 50 micrometers that is 10 cm in length can be placed between the cathode 116 and the anode 114, which can have a potential difference of 1000 V. The resulting electric field in such a configuration is 100 V/cm. If the electrodes 112A-112B are spaced about 0.1 mm from one another, then a voltage difference of about 1 V corresponds to an electric field of −100 V/cm. Therefore, a voltage difference of about 1 V or more can substantially cancel the 100 V/cm electric field. In this example, the strong portion 118 of the electric field $\vec{E}$ is 111 V/cm and the weak portion 120 of the electric field $\vec{E}$ is about 0 V/cm. Similar calculations can be used to determine the appropriate voltages and electrode spacing to result in desired field strengths. For example, the strong portion 118 of the electric field $\vec{E}$ can be at least 1,000 V/m or 30,000 V/m or more.

Although the microcapillary devices 10 and 100 in FIGS. 1A and 1B, respectively, are illustrated with high dielectric rings 12 and electrodes 112A-112B, it should be understood that other configurations for reducing the electric field and/or providing a non-uniform electric field along the length of a microcapillary tube are possible. For example, high dielectric components can be spaced apart along the length of the microcapillary tube forming circumferential rings around the outer surface of the microcapillary tube. Alternatively, the high dielectric components may be positioned near one portion of the microcapillary tube without forming a ring around the entire circumference of the tube. In some embodiments, an array of microcapillary tubes can be formed. High dielectric components can be positioned around the circumference of each tube in the array, or, alternatively, high dielectric components can be positioned adjacent multiple microcapillary tubes in the array so that one high dielectric component can create a reduced electric field in more than one of the microcapillary tubes. In some embodiments, electrodes can be used in place of the high dielectric components. For example, electrical wires can be wrapped around the microcapillary tube.

Figure 3:
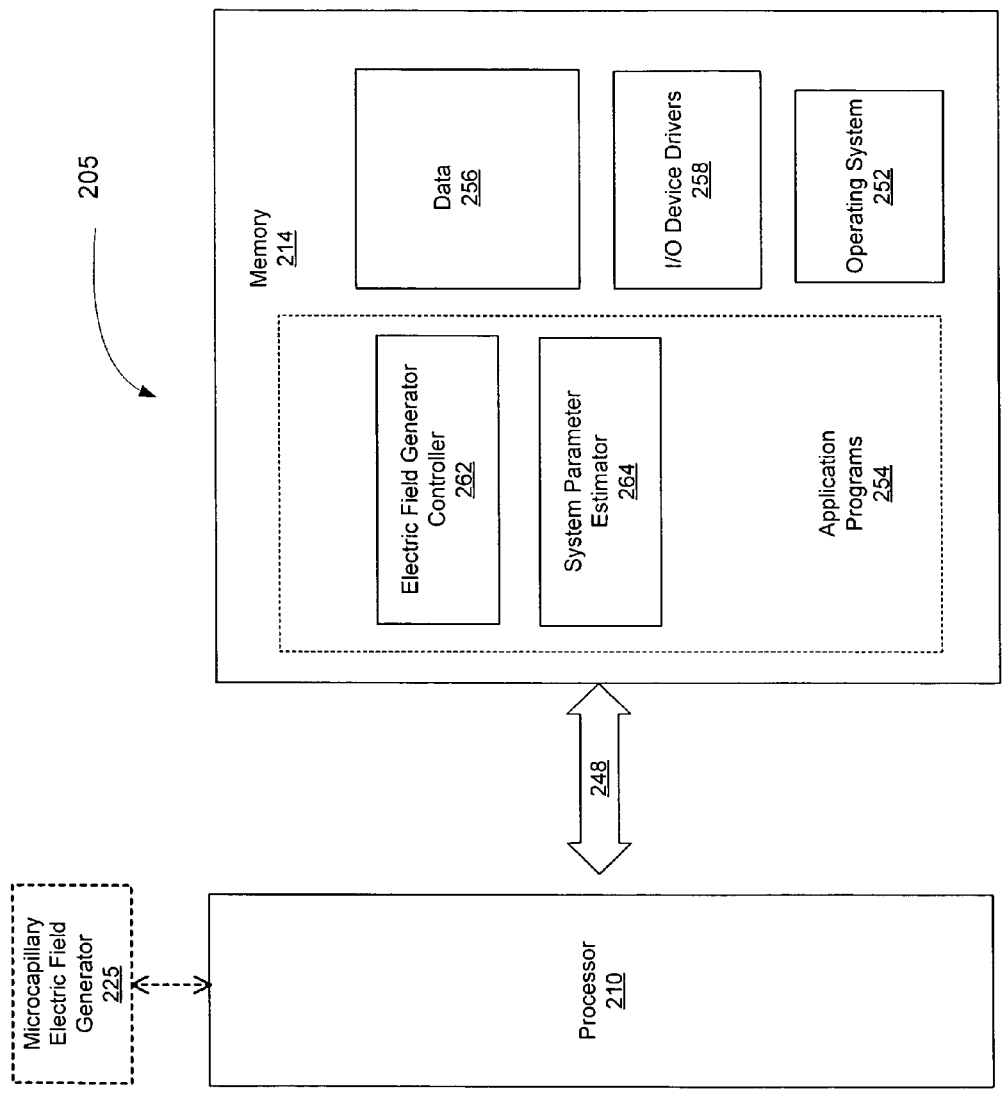
FIG. 3 is a data processing system according to embodiments of the present invention.

FIG. 3 is a block diagram of exemplary embodiments of data processing systems that illustrates systems, methods, and computer program products in accordance with embodiments of the present invention. A data processing system 205 includes a processor 210 that can send and receive information to and/or from a microcapillary electric field generator 225. The data processing system 205 and the microcapillary electric field generator 225 can be provided as separate components or two or more systems or system components can be provided as an integrated system.

As illustrated, the processor 210 communicates with the memory 214 via an address/data bus 248. The processor 210 can be any commercially available or custom microprocessor. The memory 214 is representative of the overall hierarchy of memory devices containing the software and data used to implement the functionality of the data processing system 205. The memory 214 can include, but is not limited to, the following types of devices: cache, ROM, PROM, EPROM, EEPROM, flash memory, SRAM, and DRAM. The memory 214 may include several categories of software and data used in the data processing system 205: an operating system 252; application programs 254; input/output (I/O) device drivers 258, and data 256.

As will be appreciated by those of skill in the art, the operating system 252 may be any operating system suitable for use with a data processing system, such as OS/2, AIX, OS/390 or System390 from International Business Machines Corporation, Armonk, N.Y., Windows CE, Windows NT, Windows95, Windows98, Windows2000 or WindowsXP from Microsoft Corporation, Redmond, Wash., Unix or Linux or FreeBSD, Palm OS from Palm, Inc., Mac OS from Apple Computer, or proprietary operating systems. The I/O device drivers 258 typically include software routines accessed through the operating system 252 by the application programs 254 to communicate with devices such as I/O data port(s), data 256 and certain components of memory 214 components and the microcapillary electric field 225. The application programs 254 are illustrative of the programs that implement the various features of the data processing system 205 and preferably include at least one application which supports operations according to embodiments of the present invention. The data 256 represents the static and dynamic data used by the application programs 254, the operating system 252, the I/O device drivers 258, and other software programs that may reside in the memory 214.

As shown in FIG. 3, the application programs 254 can include an electric field generator controller 262 and a system parameter estimator 264. The electric field generator controller 262 can control the operation of the microcapillary electric field generator 225. For example, the electric field generator controller 262 can control the length of $t_{on}$ and $t_{off}$ and the strength of the generated electric field. The system parameter estimator 264 can estimate system parameters, such as $t_{on}$, $t_{off}$, $S_1$, $S_2$, electric field strength, coefficients of friction for an analyte of interest, and the like. For example, a user could input the analytes of interest to the system parameter estimator 264. The system parameter estimator 264 can then calculate approximations of optimal system parameters to select $t_{on}$, $t_{off}$, S1, S2, and/or the electric field strength. A user can then select and/or build a microcapillary configuration having the appropriate parameters. For example, calculated approximations of the distances S1, S2 can be used to build a device having the calculated dimensions. Alternatively, the calculated values from the system parameter estimator 264 can be used by the electric field generator controller 262 to control the operation of the electric field generator 225 without requiring intervention by the user. For example, for any given S1, S2 and analyte diffusion coefficients, the system parameter estimator 264 can calculate approximations of optimal values for $t_{on}$ and $t_{off}$. The electric field generator controller 262 can switch the electric field generated by the electric field generator 225 on and off for durations $t_{on}$ and $t_{off}$, respectively.

Although the present invention is illustrated in FIG. 3, for example, with reference to the electric field generator controller 262 and the system parameter estimator 264 as examples of application programs 254 in FIG. 3, as will be appreciated by those of skill in the art, other configurations may also be utilized. For example, the electric field generator controller 262 and the system parameter estimator 264 may also be incorporated into the operating system 252, the I/O device drivers 258 or other such logical division of the data processing system 205. Thus, the present invention should not be construed as limited to the configuration of FIG. 3, which is intended to encompass any configuration capable of carrying out the operations described herein.

The I/O device drivers 258 can be used to transfer information between the data processing system 205 and the microcapillary electric field generator 225, or another computer system or a local or global network (e.g., the Internet) or to other devices controlled by the processor. These components may be conventional components such as those used in many conventional data processing systems that may be configured in accordance with the present invention to operate as described herein.

Operations that can be performed, for example, using the microcapillary device 10 of FIG. 1A and/or the data processing system 205 of FIG. 3 are shown in FIGS. 4 and 5. High dielectric components are positioned along a microcapillary tube at Block 302. The microcapillary tube can then be filled with an analyte solution at Block 304. An electric field along the length of the microcapillary tube can be generated at Block 306. The high dielectric components can selectively reduce the electric field at spatial intervals along the length of the microcapillary tube. The electric field can be switched on and off at Block 308 to separate analytes of interest in the solution. The electric field is preferably toggled between active and inactive states in order to separate various analytes in the solution.

Referring to FIG. 5, a microcapillary tube can be filled with an analyte solution at Block 402. A non-uniform electric field can be generated along the length of the microcapillary tube at Block 404. An exemplary non-uniform electric field is shown in FIG. 1A in which high dielectric rings 12 selectively reduce the electric field at spatial intervals along the length of the tube 30. The non-uniform electric field is then switched on and off to separate a plurality of analytes in the solution at Block 406.

Figure 6:
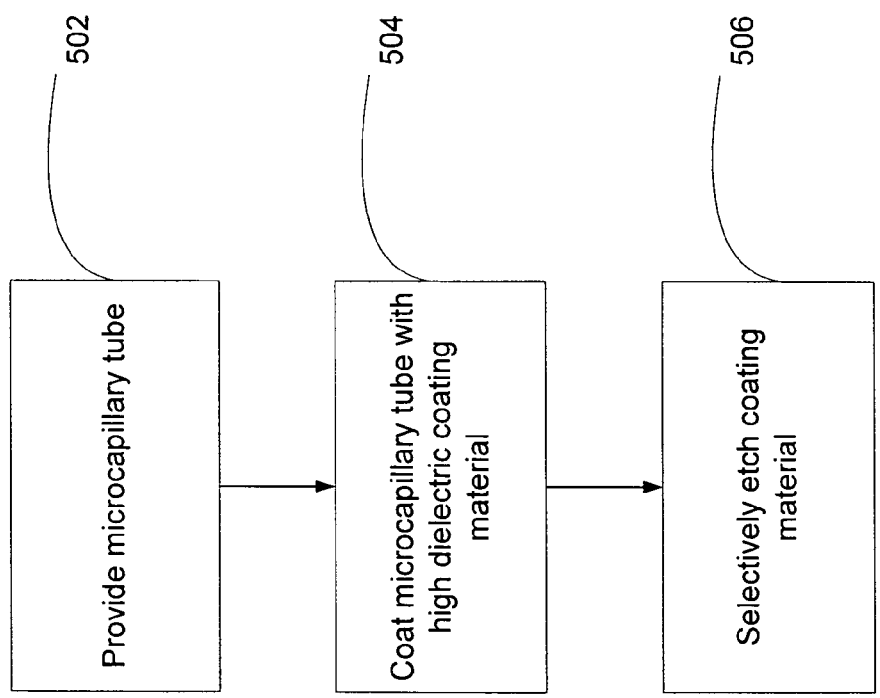

Exemplary methods of manufacturing microcapillary tubes according to embodiments of the invention are shown in FIG. 6. A microcapillary tube is provided in Block 502 and the microcapillary tube is coated with a high dielectric coating material at Block 504. Examples of high dielectric coating materials include strontium titanate and/or barium titanate. The coating material can then be selectively etched to provide a plurality of high dielectric components, such as the rings 12 shown in FIG. 1A or the electrodes 112 in FIG. 1B. The components can be spaced apart along the length of the tube so that a nonuniform electric field is provided when the tube is placed between an electric potential.

The following non-limiting examples are provided to further illustrate embodiments of the present invention.

EXAMPLE 1

Without wishing to be bound by any particular theory, the probability of motion of a particle in the microcapillary in the absence of an electric field $\vec{E}$ can be described as follows. When the electric field and the electroosmotic fluid flow are inactive, there is no net force on an analyte in the microcapillary. A particle starting at time t=0 at position x=0 may be found between positions $x_1$ and $x_2$ with a probability:

$$p = \int_{x_1}^{x_2} P(x, t) dx \qquad \text{Eq (1)}$$

where $$P(x, t) = \frac{1}{\sqrt{4\pi Dt}} \exp\left[-\frac{x^2}{4Dt}\right] \qquad \text{Eq (2)}$$

and P(x,t) describes a spreading Gaussian.

In some embodiments, $t_{on}$ is selected so that the duration of $t_{on}$ is sufficient for substantially all analytes to migrate to the energy minimum, i.e., stable positions 24A-24C in FIGS. 1A and 2. If the starting position of the analyte when the electric field $\vec{E}$ is turned "on" is in one of the regions B, D and F in FIG. 2, the force on the analyte in an electric field can be described by the following equations:

$$F_1 = \beta v_1 \qquad \text{Eq(3)}$$

where $v_1$ is the velocity of the analyte and $\beta$ is the coefficient of friction. Assuming that $t_{on}$ is a sufficient duration so that the analyte can travel the distance of $S_1$ in FIG. 1A, the velocity $v_1$ is the distance $s_1$ divided by $t_{on}$. Therefore, the force can be expressed as follows:

$$F_1 = \beta \frac{S_1}{t_{on}} \qquad \text{Eq (4)}$$

and $$t_{on} > \frac{\beta S_1}{F_1}$$

The coefficient of friction, $\beta$, is related to the diffusion coefficient, D, by Einstein's Fluctuation-Dissipation Theorem:

$$\beta = \frac{kT}{D} \qquad \text{Eq (5)}$$

where T is the temperature and k is Boltzmann's constant. In some embodiments, the distance $S_2$ in FIG. 1A and $t_{off}$ are selected such that the Gaussian spread of the diffusion probability has a standard deviation of about the length of $S_2$:

$$<S_2^2> = 2Dt_{off} \qquad \text{Eq(6)}$$

According to Equation 6, $t_{off}$ is independent of electric field, flow speed, or other equipment parameters. Generally, $t_{off}$ may be the factor that limits the speed of separation. Taking smaller spatial periods can increase the rate of separation.

An electric field generator, such as the electric field generator 225 and the electric field generator controller 262 of FIG. 3, controls the electric potential between the anode 14 and the cathode 16 in the microcapillary device 10 in FIG. 1A. In this example, one cycle of the electric field lasts $T = t_{on} + t_{off}$. The probability of a forward step (e.g., movement between the stable positions 24A-24C to the left in FIGS. 1A and 2) after one cycle is $p_f$, and the probability of a backward step (e.g., movement between the stable positions 24A-24C to the right in FIGS. 1A and 2) after one cycle is $p_b$. The values of $p_f$ and $p_b$ can be calculated by integrating the Gaussian in Equation 2 with respect to the position, x, and includes error functions, as discussed below. In the course of many successive periods, T, a group of analyte molecules that start at the same time at the same point travels along the array of stable positions 24A-24C as a drifting and spreading Gaussian.

EXAMPLE 2

The system described in Example 1 is used to derive drift and diffusion of an analyte in terms of $p_f$ and $p_b$. An estimate for how long the electric field between the anode 14 and the cathode 16 is switched on and off and how long an array of stable positions 24A-C the device should preferably have in order for two sample analytes to be separated into two distinct spreads. The following calculations can be performed by the system parameter estimator 264. In particular, the calculations in this example were performed using Mathematica™; however, other suitable calculations and/or computer programs can be used. In this example, the length of the short and long segments ($S_1$ and $S_2$) and the diffusion coefficients of two exemplary analytes are input to the system parameter estimator 264. The system parameter estimator 264 calculates an order-of-magnitude estimate for $t_{off}$ and the associated $p_f$ and $p_b$. The system parameter estimator 264 can also estimate the $t_{off}$ that may result in the shortest duration to separate the two analytes. The minimum number of spatial periods or stable positions 24A-24C used in the device 10 may also be calculated.

Standard Deviation Calculation

In this example, the length between steps is $L = S_1 + S_2 = 1$. In every period, T, a particle in the microcapillary tube can move forward (+1 with a probability of $p_f$), backward (−1 with a probability of $p_b$) or remain in the same position (0 with a probability of $1 - p_f - p_b$). The drift speed for such a particle is $<v> = p_f(+1) + p_b(-1) = p_f - p_b$. If the length between steps is L for a period of T, the drift speed is as follows:

$$<v> = \frac{(p_f - p_b)L}{T} \qquad \text{Eq (7)}$$

After the system runs for some number of periods T for τ second, the covered distance averages:

$$\Lambda = (p_f - p_b)L(\tau/T) \qquad \text{Eq(8)}$$

To calculate the variance, in one period T for T=1, L=1, the average displacement is $<X> = p_f - p_b$. In the second period, the average displacement is as follows:

$$<X^2> = p_f(+1)^2 + p_b(-1)^2 = p_f + p_b \qquad \text{Eq(9)}$$

The variance can be derived as follows:

$$\sigma^2 = <X^2> - <X>^2 = p_f + p_b - (p_f - p_b)^2 \qquad \text{Eq(10)}$$

or $$\sigma^2_{(L=1)} = p_f(1-p_f) + p_b(1-p_b) + 2p_f p_b \qquad \text{Eq(11)}$$

To determine the variance for any L, the variance can be multiplied by $L^2$. Variances are cumulative, and therefore, after running the system for τ seconds, the variance is as follows:

$$\sigma^2 = \{p_f(1-p_f) + p_b(1-p_b) + 2p_f p_b\} L^2 \left(\frac{\tau}{T}\right) \qquad \text{Eq (12)}$$

The standard deviation is the square root of the variance, i.e., σ.

Time Period Calculation

If there are two analytes in the microcapillary tube, after the system has been activated for τ seconds, the difference in average covered distance for the two analytes can be expressed as follows:

$$\Lambda_1 - \Lambda_2 = \{(p_{f1} - p_{b1}) - (p_{f2} - p_{b2})\} L(\tau/T) \qquad \text{Eq(13)}$$

In order for the analytes to separate, the difference in the equation above is preferably greater than the sum of the standard deviations ($\sigma_1 + \sigma_2$) or, in other words, $$\frac{\Lambda_1 - \Lambda_2}{\sigma_2 + \sigma_2} > 1. \qquad \text{Eq (14)}$$

Therefore, an estimate for the minimum time that the device should be activated in order to have sufficient separation between the analytes can be expressed as follows:

$$\tau > \left\{ \frac{\sigma_1 + \sigma_2}{(p_{f1} - p_{b1}) - (p_{f2} - p_{b2})} \right\} T \qquad \text{Eq (15)}$$

and (τ/T) is an estimate of the minimum number of time periods to bring about a separation between the analytes. An estimate for the minimum number of spatial periods (i.e., the minimum number of high dielectric rings or sets of stable/unstable positions in the microcapillary tube) is the product of ($\tau/T$) and the larger of either the difference between $p_{f1}$ and $p_{b1}$ or the difference between $p_{f2}$ and $p_{b2}$, i.e., Max[($p_{f1}-p_{b1}$), ($p_{f2}-p_{b2}$)]. Multiplying the number of spatial periods with the spatial period length L yields the minimum length of microcapillary tubing.

EXAMPLE 3

In this example, the high dielectric rings 12 in FIG. 1A are 0.1 micrometers wide ($S_2$) and are placed 0.9 micrometers apart ($S_1$) along the microcapillary tube 30. Two DNA strands in an aqueous solution are placed in the microcapillary tube 30. The DNA strands have lengths of 1000 units and 1001 units. The diffusion coefficient of an analyte is generally proportional to the square root of its length. Therefore, the diffusion coefficients for the two DNA strands are estimated as follows:

$$D_{f1}=\sqrt{1000}=31.62\times 10^{-11}\ m^2/sec$$

$$D_{f2}=\sqrt{1001}=31.64\times 10^{-11}\ m^2/sec \qquad Eq(16)$$

The average time that it takes a molecule with a diffusion coefficient D to diffuse a given distance is shown in Equation 6, which can be rewritten as follows:

$$t_{off} = \frac{<S_2^2>}{2D} \qquad Eq\ (17)$$

Therefore, the $t_{off}$ for the slowest diffusing (or largest) DNA strand is $t_{off}=(0.1\ \mu m)^2/2(31.64\times 10^{-11})=1.581\times 10^{-5}$ s.

Figure 7:
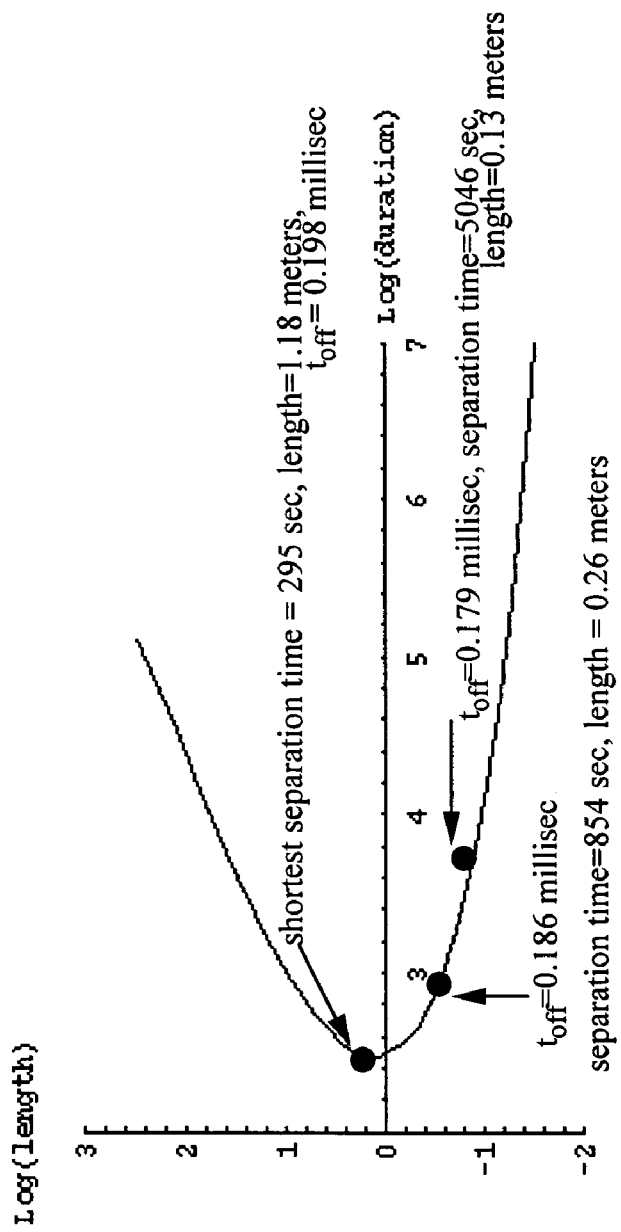
FIG. 7 is graph showing the logarithm of the total length of the microcapillary tube and the logarithm of the total amount of time that may be needed to separate two DNA strands having lengths of 1000 and 1001 units for various $t_{off}$ according to embodiments of the present invention.

The minimum time that it takes the two DNA strands to separate and the minimum length of microcapillary tubing needed is then calculated using Equation 14 for $t_{off}=1.58128\times 10^{-5}$ s and other values of $t_{off}$ as illustrated in FIG. 7. In this example, an arbitrary initial $t_{off}$ is chosen as a value much lower than the calculated $t_{off}=1.58126\times 10^{-5}$ s, for example, $t_{off}=1.58126\times 10^{-5}$ s÷40. The minimum time of separation and minimum length of tubing is then calculated for the initial $t_{off}$. These calculations are repeated successively by increasing $t_{off}$ by 2% for each iteration.

As illustrated in FIG. 7, the "optimum" $t_{off}$ is $1.98\times 10^{-4}$ seconds. By decreasing $t_{off}$, the minimum total separation time increases; however, the minimum length of the microcapillary tubing is decreased. For example, at $t_{off}=1.98\times 10^{-4}$ seconds, the separation time is 295 seconds (about 5 minutes) and requires 1.18 meters of microcapillary tubing. However, at $t_{off}=1.87\times 10^{-4}$ seconds, the minimum separation time is 854 seconds (about 15 minutes) and only 0.29 meters of microcapillary tubing is needed. Large lengths of microcapillary tubing may be difficult to manufacture and/or hard to work with. Therefore, the values in FIG. 7 can be used to select a feasible length of microcapillary tubing having an acceptable separation time.

If the diffusion coefficients used in FIG. 7 were 10 times as small, i.e., $D_{f1}>=31.62\times 10^{-12}$ and $D_{f2}=31.64\times 10^{-12}$, then the corresponding values of $t_{off}$ and total separation times are ten times as large; however, the length of the microcapillary tube is the same. For example, the "optimum" $t_{off}$ is $1.98\times 10^{-3}$ seconds and the minimum time for the DNA strands to separate is 2952 seconds (50 minutes). At $t_{off}=1.87\times 10^{-3}$ seconds, the minimum separation time is 8540 seconds (about 150 minutes); however, only 0.29 meters of microcapillary tubing is needed.

EXAMPLE 4

The calculations described above were used to calculate parameters for a microcapillary tube with $S_1=0.9$ mm and $S_2=0.1$ mm. This device may be effective for separating fairly small molecules with high diffusion coefficients. In this example, an amino acid has an estimated diffusion coefficient of $D_{f1}=9.0\times 10^{-10}$ $m^2$/sec and a dipeptide of the same amino acid has a diffusion coefficient of $D_{f2}=6.0\times 10^{-10}$ $m^2$/sec. These values can be used to generate a graph or table of the values of minimum separation time, minimum microcapillary length, and $t_{off}$. In this example, the minimum separation time is about 310 seconds (about 5 minutes) using a 0.0056 meter microcapillary tube and $t_{off}$ is 71.0 seconds. If the value for $t_{off}$ is 66.9 seconds, separation takes 796 seconds (about 13 minutes) and the minimum microcapillary tubing length is about 0.0022 meters.

In the drawings and specification, there have been disclosed exemplary embodiments of the invention and, although specific terms are employed, they are used in a generic and descriptive sense only and not for purposes of limitation, the scope of the invention being set forth in the following claims.

What is claimed is:

1. A method of separating analytes in a microcapillary tube, the method comprising:
   positioning a plurality of electric field reducing components spaced apart along a length of a microcapillary tube,
   filling the microcapillary tube with an analyte solution;
   generating an electric field along the length of said microcapillary tube, the plurality of electric field reducing components selectively reducing the electric field at spatial intervals along the length of the microcapillary tube; and
   switching the electric field on and off to separate a plurality of analytes in the analyte solution along a length of the microcapillary tube, wherein the plurality of analytes freely diffuse when the electric field is off such that a net force on the plurality of analytes is approximately zero.

2. The method of claim 1, wherein the plurality of electric field reducing components includes a plurality of high dielectric components having a dielectric constant greater than about 80.

3. The method of claim 2, further comprising forming the plurality of high dielectric components of strontium titanate.

4. The method of claim 2, further comprising forming the plurality of high dielectric components of a material having a dielectric constant of at least about 100.

5. The method of claim 2, further comprising forming the plurality of high dielectric components in a series of circumferential rings around an outer surface of the microcapillary tube.

6. The method of claim 1, wherein the plurality of electric field reducing components comprise a plurality of electrodes.

7. The method of claim 6, wherein the plurality of electrodes include electrically conducting wires forming circumferential rings around an outer surface of the microcapillary tubes.

8. The method of claim 1, wherein said switching step comprises activating the electric field for an activation duration of between about 0.1 ms and about 100 seconds and deactivating the electric field for a deactivation duration of between about 0.1 ms and about 100 seconds.

9. The method of claim 1, wherein said generating step comprises generating the electric field at a voltage of at least about 1,000 V/m.

10. The method of claim 1, wherein said generating step comprises generating the electric field at a voltage of at least about 30,000 V/m.

11. The method of claim 1, wherein the analyte solution comprises an aqueous fluid and a plurality of analytes selected from the group consisting of nucleic acids, amino acids, peptides, proteins, nucleosides and nucleotides, small organic compounds, inorganic ions, organic acids, vitamins, steroids, carbohydrates, hormones or drugs, and cells.

12. The method of claim 1, wherein said microcapillary tube has a diameter of about 50 μm, said plurality of electric field reducing components has a length along a primary axis of said microcapillary tube of about 0.1 mm, and said plurality of electric field reducing components are separated by about 0.9 mm.

13. The method of claim 1, further comprising calculating the minimum number of the plurality of electric field reducing components to separate two or more of the plurality of analytes.

14. The method of claim 1, further comprising, calculating the minimum number of periods in which the electric field is switched on and off to separate two or more of the plurality of analytes.

15. The method of claim 1, wherein switching the electric field on and off separates the plurality of analytes in the analyte solution along a straight line along the length of the microcapillary tube.

16. The method of claim 1, wherein when the electric field is on, electroosmotic flow in the microcapillary tube and the electric field together produce a net force on analytes in the microcapillary tube such that the net force in a first plurality of regions in the microcapillary tube is in a first direction and the net force in a second plurality of regions in the microcapillary tube is in a second direction that is opposite the first direction.

17. A method of separating analytes in a microcapillary tube, the method comprising:
   filling a microcapillary tube with an analyte solution;
   generating a non-uniform electric field along a length of a microcapillary tube; and
   switching the non-uniform electric field on and off to separate a plurality of analytes in the analyte solution, wherein the plurality of analytes freely diffuse when the electric field is off such that the net force on the plurality of analytes is approximately zero.

18. The method of claim 17, wherein said generating comprises positioning electrodes along the length of the microcapillary tube.

19. The method of claim 18, wherein the electrodes are wire rings configured to circumferentially surround the microcapillary tube.

20. The method of claim 17, wherein said generating comprises positioning high dielectric components along the length of the microcapillary tube.

21. The method of claim 17, wherein switching the electric field on and off separates the plurality of analytes in the analyte solution along a straight line along the length of the microcapillary tube.

22. The method of claim 17, when the electric field is on, electroosmotic flow in the microcapillary tube and the electric field together produce a net force on analytes in the microcapillary tube such that the net force in a first plurality of regions in the microcapillary tube is in a first direction and the net force in a second plurality of regions in the microcapillary tube is in a second direction that is opposite the first direction.

* * * * *